Sept. 14, 1954 R. S. MOORE Plant Pat. 1,301

MINIATURE ROSE PLANT

Filed June 5, 1953

WITNESS

Addison E. Avery

INVENTOR

Ralph S. Moore

Webster & Webster

ATTYS.

Patented Sept. 14, 1954

Plant Pat. 1,301

UNITED STATES PATENT OFFICE 1,301

MINIATURE ROSE PLANT

Ralph S. Moore, Visalia, Calif.

Application June 5, 1953, Serial No. 359,979

1 Claim. (Cl. 47—61)

This invention is directed to a new and distinct variety of miniature rose plant; such plant bearing general resemblance to the Oakington Ruby (unpatented), the seed parent, but being advantageously distinguishable therefrom by darker red buds and flowers; somewhat darker foliage; very double flowers; and greater fragrancy.

The instant variety is additionally characterized by excellent form; ease of propagation; bright color; hardiness; and a free flowering habit.

Still further characteristics of this variety of miniature rose plant are that it is thornless and does not bear seeds.

The plant of the present variety is of dwarf type, bushy, being upright at first and then becoming well rounded to spreading at maturity; the average height at maturity being ten to twelve inches, with flowers which—when fully open—average an inch to an inch and a quarter in diameter.

The present variety of miniature rose plant is well adapted for greenhouse or outdoor propagation, growing strenuously and vigorously in either adaptation; the variety being well adapted for use as a pot plant, or for garden ornamentation.

The present variety of rose plant was originated by me in my experimental nursery at Visalia, county of Tulare, State of California, during the course of extensive breeding of miniature roses to obtain varieties best suited for commercialization in the trade; the variety herein claimed being a seedling of the Oakington Ruby, open-pollinated. Such seedling was carefully observed by me during its growth, and when it reached maturity and bore flowers it had general resemblance to the seed parent, Oakington Ruby, but I recognized that it had especially desirable and distinctive features, as described herein.

Subsequent to its origination, as above, the variety was selected by me for propagation and was successfully asexually reproduced in my nursery by means of cuttings. These cuttings, of which there were a number, grew to maturity, and were found to carry forward each and every one of such desirable characteristics of the initial plant.

Figure 2:
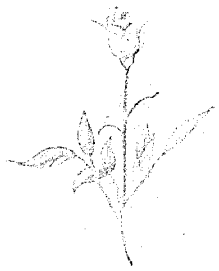
Fig. 2 is a similar view of a single bud, with its stems and leaves.
Figure 1:
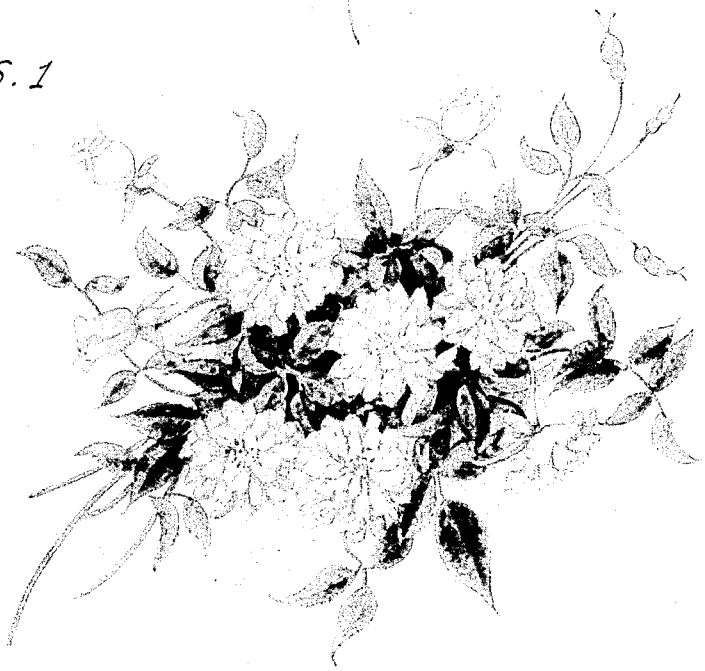
Fig. 1 is a perspective of a cluster of the flowers, together with buds, leaves, and stems.
Figure 3:
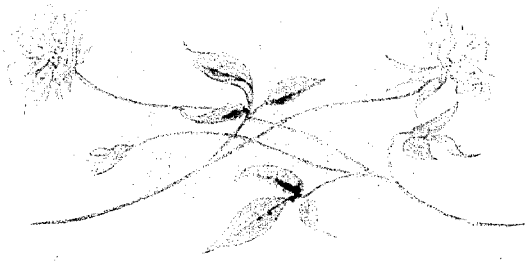
Fig. 3 is a similar view of a pair of the flowers in full bloom, with stems and leaves.

Referring now specifically to the new and distinct variety of rose plant, the following is a detailed description thereof in outline; all major color plate identifications being by Maerz and Paul Dictionary of Color:

Type: Dwarf; bush; greenhouse; outdoor; garden decoration; pot plant.

Class: Miniature.

Flowers:

*Continuity.*—Continuous.

*Fragrance.*—Moderate; spicy.

Flowers borne: Singly. Several to stem. Normal, medium length stems.

Quantity of bloom: Abundant in greenhouse and outdoors.

Bud:

*Peduncle.*—Medium length; slender; medium erect; medium green; almost smooth; few red hairs; very tiny, almost non-existent prickles.

*Before calyx breaks.*—Size—small. Form—pointed; without foliaceous appendages on the surface of the bud; without foliaceous parts extending beyond the tip of the bud. Color—medium green.

*As calyx breaks.* — Color — bud — medium green. Flower—red.

*As first petal opens.*—Size—small. Form—long; pointed. Color—outside and inside—variable dark red, shading to as deep as 53–L–12. Opening—opens well.

Bloom:

*Size.*—When fully open—very small, 1 inch to 1¼ inch.

*Petalage.*—Very double, with sixty to seventy petals arranged irregularly.

*Form.*—Full, high center at first, becoming almost ball shaped; petals at first, and at maturity, rolled outwardly.

Petals: Soft. Inside—velvety. Outside—satiny.

*Shape.*—Outside—obovate. Intermediate—lanceolate. Inside—lanceolate.

*Color.*—Outer petals—variable dark red, shading from 53–K–10 to as deep as 53–L–11 or 12. Inner petals—slightly lighter red, shading from 52–J–9 to the darker shades of the outer petals.

The color of all petals appears to lighten somewhat on flowers open several days; numerous petals having a whitish tinge toward the center of the flower.

Reproductive organs:

*Stamens.*—Few. Arranged irregularly about pistils. Mixed with petaloids.

*Filaments.*—Short; few; most with anthers; white.

*Anthers.*—Small; open at various times; yellow.
*Pollen.*—Sparse; yellow.
*Pistils.*—Medium.
*Styles.*—Even; short; very thin; bunched.
*Stigma.*—Red.
*Ovaries.*—All enclosed in calyx.
*Hips.*—None.
*Sepals.*—Light green—falls off with old flower.
*Seeds.*—None.

*Plant*

Foliage:
*Leaves.*—Compound of 5 to 7. Normal; small; moderately heavy; glossy.
*Leaflets.*—Oval, with apex acute. Base round.
*Color.*—Leaves: upper surface—normal green (23-L-27); under surface, and young leaves (both surfaces), somewhat lighter.
*Rachis.* — Light. Upper side — smooth, grooved. Under side—sparsely thorny.
*Stipules.*—Short. Narrow; with short points, turning out at an angle of less than 45°.
Growth:
*Habit.*—Dwarf; bushy; branched.
*Growth.*—Free; vigorous.
*Canes.*—Medium.
*Main stems.*—Green to bronze red outdoors.

Thorns—none. Prickles—none. Hairs—none.
*Branches.*—Green to bronze red outdoors. Prickles—none. Hairs—none.
*New shoots.*—Green. Prickles—none. Hairs—none.

The miniature rose plant and its flowers as herein described may vary in slight detail due to climatic and soil conditions under which the variety may be grown, particularly as to flower color, which may vary somewhat, dependent on the age of wood from which the shoots arise; the extent of fertilization of the soil; and the temperature under which the plant is grown.

Having thus described my invention, I claim:

A new and distinct variety of miniature rose plant bearing general resemblance to the seed parent, Oakington Ruby, but distinctively characterized therefrom by darker red buds and flowers, somewhat darker foliage, more double flowers, and greater fragrancy; the variety being additionally characterized by a free flowering habit, a bushy plant upright at first and then becoming well rounded to spreading, with an average height at maturity of ten to twelve inches, and an average size bloom of one to one and one-quarter inches in diameter; and a plant which has no thorns and bears no seeds.

No references cited.